United States Patent
Boeck et al.

(10) Patent No.: US 9,334,215 B2
(45) Date of Patent: May 10, 2016

(54) METHOD FOR REMOVING ACROLEIN FROM THE PROCESS GAS OF A HETEROGENEOUSLY CATALYSED OXIDATION OF PROPENE

(71) Applicants: Wolfgang Boeck, Langenselbold (DE); Wolfgang Taugner, Gelnhausen (DE); Udo Gruber, Darmstadt (DE)

(72) Inventors: Wolfgang Boeck, Langenselbold (DE); Wolfgang Taugner, Gelnhausen (DE); Udo Gruber, Darmstadt (DE)

(73) Assignee: EVONIK DEGUSSA GmbH, Essen (DE)

( * ) Notice: Subject to any disclaimer, the term of this patent is extended or adjusted under 35 U.S.C. 154(b) by 0 days.

(21) Appl. No.: 14/762,124

(22) PCT Filed: Jan. 28, 2014

(86) PCT No.: PCT/EP2014/051573
§ 371 (c)(1),
(2) Date: Jul. 20, 2015

(87) PCT Pub. No.: WO2014/122044
PCT Pub. Date: Aug. 14, 2014

(65) Prior Publication Data
US 2015/0353460 A1    Dec. 10, 2015

(30) Foreign Application Priority Data

Feb. 6, 2013  (EP) .................................... 13154227

(51) Int. Cl.
*C07C 45/35* (2006.01)
*C07C 45/78* (2006.01)
*C07C 45/82* (2006.01)

(52) U.S. Cl.
CPC .................. *C07C 45/35* (2013.01); *C07C 45/78* (2013.01); *C07C 45/783* (2013.01); *C07C 45/82* (2013.01)

(58) Field of Classification Search
CPC ........ C07C 45/28; C07C 45/35; C07C 45/82; C07C 45/783
USPC ........................................................ 568/476
See application file for complete search history.

(56) References Cited

U.S. PATENT DOCUMENTS

| | | |
|---|---|---|
| 3,926,744 A | 12/1975 | Noll et al. |
| 5,866,721 A | 2/1999 | Hofen et al. |
| 5,886,230 A | 3/1999 | Hofen et al. |
| 7,190,270 B2 | 3/2007 | Möller et al. |
| 7,326,393 B2 | 2/2008 | Moller et al. |
| 7,604,788 B2 | 10/2009 | Moller et al. |
| 2003/0187299 A1 | 10/2003 | Machhammer et al. |
| 2015/0353460 A1 | 12/2015 | Boeck et al. |

FOREIGN PATENT DOCUMENTS

| | | |
|---|---|---|
| DE | 2 263 496 A1 | 7/1974 |
| WO | 01/96271 A2 | 12/2001 |

OTHER PUBLICATIONS

International Search Report Issued Mar. 3, 2014 in PCT/EP14/051573 Filed Jan. 28, 2014.
European Search Report Issued Jun. 21, 2013 in European Application No. 13154227.6 Filed Feb. 6, 2013.

*Primary Examiner* — Sikarl Witherspoon
(74) *Attorney, Agent, or Firm* — Oblon, McClelland, Maier & Neustadt, L.L.P.

(57) ABSTRACT

The invention relates to a process for separating acrolein from the process gas of a heterogeneously catalyzed oxidation of propene by means of atmospheric oxygen, wherein high boilers (including acrylic acid) are firstly separated off from the process gas by means of quenching and technical-grade acrolein having small proportions of low boilers is then obtained by means of absorption and subsequent distillation. Small amounts of a solvent by means of which, in particular, oligomers formed are separated off and the tendency for foam to be formed in the apparatuses or columns is reduced is added in the columns and heat exchangers in the work-up process. The solvent is, according to the invention, separated off and recycled in the form of an organic phase in-situ within the existing process.

23 Claims, 4 Drawing Sheets

Figure 1

Figure 2

Comparative Example 1

Figure 4:
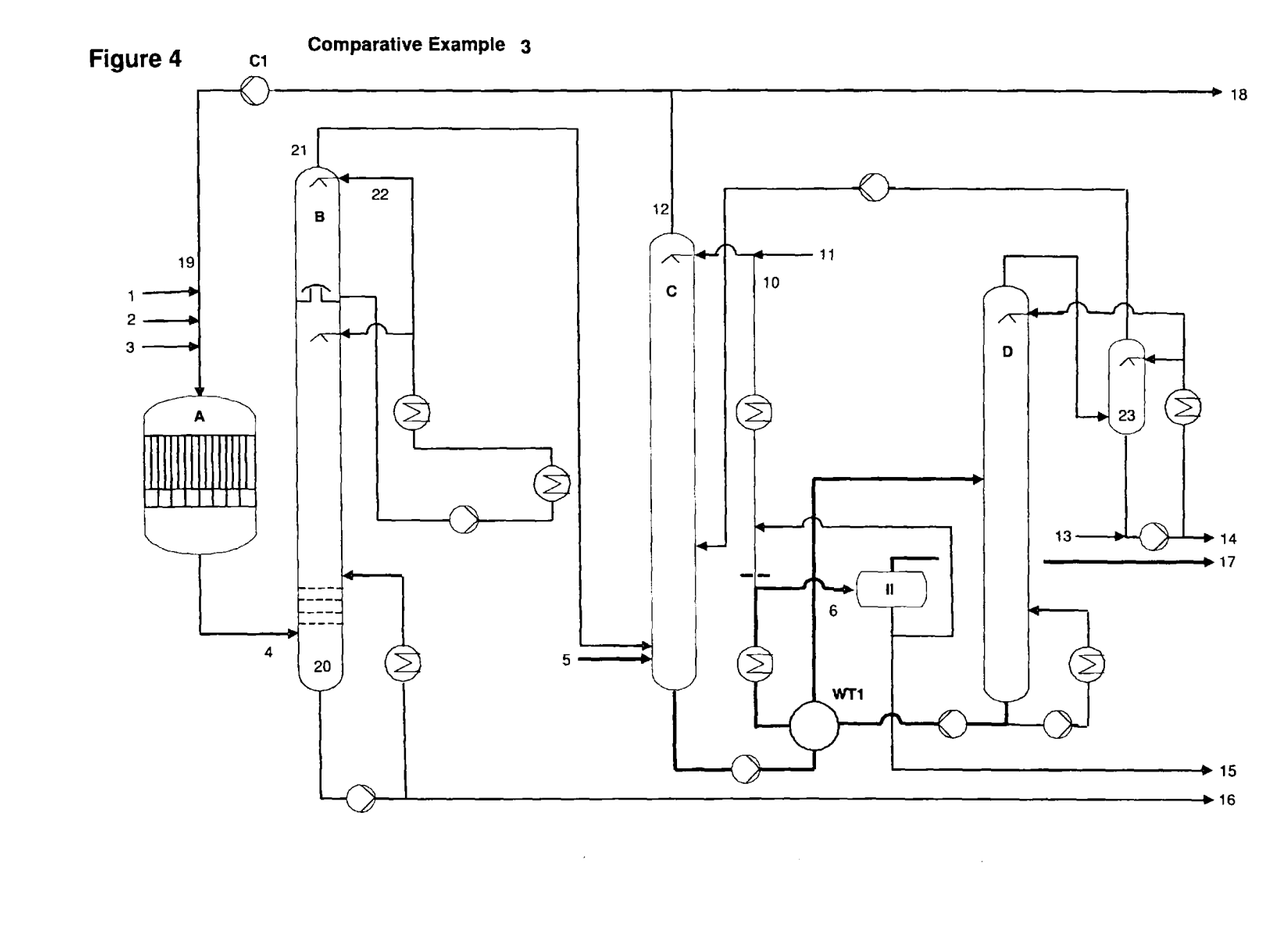

Figure 4    Comparative Example 3

METHOD FOR REMOVING ACROLEIN FROM THE PROCESS GAS OF A HETEROGENEOUSLY CATALYSED OXIDATION OF PROPENE

The heterogeneously catalyzed oxidation of propene by means of atmospheric oxygen according to the present prior art is comprehensively described in the latest editions of Ullmann's Encyclopedia of Industrial Chemistry, D. Arntz et al., online edition 15 Apr. 2007, Volume 1, Wiley-VCH-Verlag und Kirk-Othmer Encyclopedia of Chemical Technology, W. G. Etzhorn, online edition 18 Dec. 2009, Volume 1, John Wiley and Sons Inc.

The oxidation of propene is carried out at elevated temperatures (300-400° C.) and slightly superatmospheric pressure over catalysts installed in shell-and-tube reactors. In addition to propene and air, steam and other inert gases are often also mixed into the feed gas in order to keep the feed gas composition outside the ignition limits. The heat of reaction is usually removed by means of liquid salt melt which circulates through the shell space of the shell-and-tube reactor. A large number of different mixed oxides systems containing molybdenum, bismuth, iron, cobalt, nickel as basis and further promoters, for example as indicated in PCT application WO 2008/046843 or WO 2008/104432, are reported as suitable catalysts. A variety of other mixed oxide systems of this type which increase the achievable acrolein yield are known from many patent documents. Both all-active catalysts (e.g. as pellets or hollow cylinders) and supported catalysts (e.g. as coated catalysts) are used here. It is common to all reaction systems that various further by-products (including acrylic acid, acetic acid, formaldehyde, acetaldehyde, allyl alcohol, $CO$, $CO_2$) are formed in addition to the target product acrolein in the oxidation reaction.

To be able to use the acrolein as starting material for further synthetic reactions, it has to be separated from this reaction mixture and purified. The basic procedure is likewise reported in the above literature references. Firstly, the reaction gas has to be cooled and the high-boiling components and water then have to be separated off from the reaction gas. The high boiler-containing wastewater obtained is usually disposed of thermally. However, other disposal routes can also be employed. The acrolein is then scrubbed (absorbed) from the process gas stream which has been prepurified in this way since condensation would be completely uneconomical because of the dilution and the low boiling point. The acrolein und the low boilers still present are distilled off from the sorbate solution obtained. The sorption liquid which has been freed of acrolein can then be reused for the absorption of acrolein. Water or a mixture of water and an organic solvent is usually used as sorption liquid.

If necessary, the acrolein can subsequently be distilled further to separate off the low boilers. From the abovementioned literature references and many other literature references, it is known that acrolein, or acrylic acid, formaldehyde or allyl alcohol, polymerize easily. Stabilizer is therefore added in the work-up section or to the acrolein itself in order to reduce the polymerization tendency. Hydroquinone, for example, has been found to be suitable for this purpose, but many other stabilizer systems have also been described. Even with addition of stabilizer, polymerization cannot be 100% prevented in the work-up section. In particular due to thermal stress in the separation of the acrolein from the sorption liquid, small amounts of oligomers are always formed and these accumulate in the sorption liquid over time and lead to the formation of polymers which then in turn cause fouling of the production facilities, necessitating cleaning.

DE 2263496 describes a process for preparing acrylic acid and acrolein, in which the acrolein- and acrylic acid-containing gas mixture coming from a catalytic gas-phase oxidation of propene is passed through a scrubbing liquid which is a mixture of water and organic liquid in order to separate off acrylic acid by extraction. The high-boiling, acrylic acid-containing aqueous/organic solution formed here is separated off as bottom phase. 2-Ethylhexanol, in particular, is used as high-boiling organic extractant. The acrylic acid is separated by distillation from the aqueous/organic solution in a plurality of work-up steps. For this purpose, water is firstly distilled off and the acrylic acid is distilled off from the remaining organic liquid and the organic liquid is then reused as scrubbing liquid. A disadvantage of the process is that relatively large amounts of solvent have to be used and circulated and have to be recovered in a complicated process, meaning a not inconsiderable energy consumption and also representing a further source of additional impurities which are formed, in particular, by reaction of the solvent with acrylic acid.

Apart from the very efficient removal of by-products from the acrolein process, it is also necessary to prevent deposition of polymeric by-products which form in the apparatuses (for example columns, column internals, heat exchangers) and pipes since these would quickly lead to a deterioration in heat transmissions or the plant throughput. This can in principle also be effected by use of water/solvent mixtures as scrubbing solution, in particular in the quenching stage, as takes place in a process according to DE 2263496. However, the disadvantage here is, in particular, the separate outlay for purification and recycling of the scrubbing solution.

On the other hand, WO 2010044990 A1 describes a process for the removal of acrylic acid from the wastewater from an acrolein process by extraction with liquefied C3 gases propylene and/or propane as extractant with the aim of recovering acrylic acid.

This process allows easy separation of the solvent from the acrylic acid-containing extraction solution by distillation, which represents an advantage over higher-boiling extractants.

Finally, WO 2001096271 discloses the preparation of acrolein starting with an absorption of propylene/propane in an organic solvent ($C_{8-20}$-alkane or alkene), in which propylene/propane is subsequently removed from the absorbent (claims 1 and 3), for example by distillation (claim 4). Entrained absorbent is subsequently scrubbed from the propylene/propane stream with water. The resulting mixture of water/organic solvent is worked up by phase separation so that the two phases are recycled into the process separately (page 59, line 1-page 60, line 8).

In terms of the economics of a production process, it is generally particularly important for the operating time between necessary stoppages for cleaning to be as long as possible and for the energy consumption during ongoing operation to be as low as possible.

Success has now been attained in reducing the proportion of acrylic acid in the acrolein process further by the use of improved catalysts as described, for example, in WO 2008/104432 or WO 2008/046843, so that a process involving use of large amounts of solvents for separating off the acrylic acid as described in DE 2263496 has become even less economically attractive.

It is therefore an object of the present invention to provide a process for separating acrolein from the process gas of a heterogeneously catalyzed oxidation of propene, which makes it possible to increase the operating time of the plant by addition of an organic solvent in the work-up section while avoiding the disadvantages of the known processes and, in particular, allows suppression of foaming in the columns and an increase in throughput in existing plants and at the same time makes possible a simple and inexpensive work-up and recycling of the solvent used.

DESCRIPTION OF THE INVENTION

According to the invention, the disadvantages of the prior art are successfully overcome by provision of a continuous process for preparing acrolein, wherein the following steps are carried out A) gas-phase oxidation of propene by means of air over a heterogeneous catalyst in the presence of a diluent gas in one reaction stage to produce an acrolein-containing gas stream (process gas), B) capture of the acrolein-containing gas stream A) in a quenching stage consisting of bottom, middle and top sections for separating off by-products in the presence of water and an organic phase containing a sparingly water-soluble organic solvent, C) capture of the acrolein-containing gas stream from the quenching stage B) in an absorption stage consisting of bottom, middle and top sections in the presence of water and an organic phase containing a sparingly water-soluble organic solvent to obtain an aqueous acrolein solution which contains organic phase, and an incondensable gas stream, C1) at least partial recirculation of the incondensable gas stream from C) as diluent gas to the reaction stage A), D) separation of the acrolein by distillation from the aqueous acrolein solution which contains organic phase from C) in a distillation stage, where the remaining aqueous solution which contains organic phase and has been freed of acrolein is discharged from the distillation stage D) so as to form an organic phase II which is separated from the associated aqueous fraction II (phase separation II), the organic phase II is introduced into the bottom section of the quenching stage B) from which the organic phase II is separated off together with an aqueous fraction via the top section by distillation and/or stripping so as to form an organic phase I which is separated from the associated aqueous fraction I (phase separation I) and introduced into the bottom section of the absorption stage C).

For the purposes of the present invention, a sparingly water-soluble organic solvent is, in particular, an organic solvent which has a solubility in water of ≤20 g/l, preferably ≤6.0 g/l, particularly preferably ≤2.0 g/l, in each case at 20° C.

When the quenching stage B) is configured as a column, a collection tray above which the outlet for the organic/aqueous phase to the phase separator I is located is preferably installed at the lower end of the top section (cf. FIG. 1), so that liquid can be discharged particularly well from the resulting intermediate liquid phase zone.

In step C1, further inert gases, for example nitrogen or steam or low-oxygen offgas from an incineration plant can also be used as diluent gas in addition to or instead of the incondensable gas stream (incondensable process gas).

The process of the invention allows, in particular as a result of the addition of an organic solvent and the organic phases formed therefrom in the work-up section, the removal of potentially polymer-forming impurities and thus an increase in the operation time of the plant and at the same time allows the solvent used to be recirculated and purified by distillation internally without an additional outlay for apparatus being required. The tendency for foaming to occur in the system, especially in the distillation stage, is also reduced. The process thus makes possible an increase in the operating time of the plant and the throughput of feed and product streams.

Preference is given to a process in which organic solvent which is sparingly water-soluble is introduced continuously or intermittently to supplement the organic phase at a suitable point in the process. This makes it possible, in particular, to keep the content of organic phase constant and thereby achieve stabilize operation.

Particular preference is also given to the organic solvent being introduced into the bottom section of the absorption stage and/or of the distillation stage. Introduction into the bottom of the absorption stage causes, in particular, the least adverse effect on the main function of the absorption stage, viz. the separation of the acrolein from the quenching gas from stage B). The organic solvent is for this purpose preferably mixed into the feed stream of organic phase to the absorption stage or introduced separately beneath this position. In the case of introduction of solvent into the bottom of the distillation stage, this measure also prevents breakthrough of the solvent or of the organic phase into the top section of the distillation stage and thus into the product acrolein.

Preference is given to using an organic solvent which has a boiling point at atmospheric pressure of from 150 to 230° C., particularly preferably from 170 to 190° C. This ensures, in particular, the discharge of the solvent from the bottom section into the top section by stripping and distillation in the quenching stage. In particular, the process gas serves as stripping gas here.

Particular preference is given to using a branched or unbranched open-chain C6-C10-alcohol, in particular 2-ethylhexanol, which is also available industrially in sufficient amounts, as organic solvent. Since the alcohols react with substances occurring in the process, e.g. with acrylic acid to form acrylic esters, i.e. in the case of 2-ethylhexanol to form 2-ethylhexyl acrylate, or with acetic acid to form 2-ethylhexyl acetate and with formaldehyde to form 2-ethylhexyl formal and 2-ethylhexyl diformal, these process products are, together with the solvent, constituents of the organic phases used according to the invention, which in this context are also referred to as solvent matrix (SM). This is even advantageous in the present process, since the solvent matrix should preferably also have a good uptake capability for oligomers and further organic by-products formed, which is particularly the case when using the organic phases formed by the alcohols mentioned.

In the process of the invention, further preference is given to a further amount of from 0.05 to 1% by weight, preferably from 0.1 to 0.5% by weight, of organic solvent, based on the amount of propene introduced into the reaction step A), being added, with preference being given to addition of such an amount of organic solvent that a constant content of organic phase is maintained. This can be checked by determining the content of organic phases, in particular the organic phase in the output stream from the phase separations, in particular the phase separation II, by known analytical methods and making adjustments accordingly. This allows a particularly advantageous and uniform mode of operation of the process of the invention and minimization of the solvent consumption.

In the process of the invention, further preference is also given to the acrolein-containing gas stream from A) going at a temperature of 200-280° C., in particular 220-250° C., into the bottom section of the corresponding step B). The process gas is for this purpose cooled appropriately in the after-cooler of the reaction step A) in order to reduce the cooling water requirement in the quenching stage. In addition, higher temperatures would increase the formation of by-products. This makes possible a mode of operation of the combination of the reaction stage A) and the subsequent quenching stage B) which is optimized in terms of energy and in respect of maximum acrolein selectivity.

In the process of the invention, further preference is given to the temperature at the bottom of the quenching stage B being set to a value in the range from 60 to 90° C. at a pressure in the top section of from 1.2 to 1.8 bar (absolute pressure) so that no separate organic phase is present in the bottom section of the quenching stage B. The discharge of the organic phase at the bottom required in the process is thus prevented and it is also ensured that the volatile components of the organic phase are transported according to the invention to the top section of the quenching stage B.

The temperature at the bottom of the quenching stage B is particularly preferably set by discharging a substream of the liquid condensed there and, after appropriate cooling, feeding it back into the lower third of the quenching stage B (lower pump circulation). Uniform introduction and temperature setting, in particular via external heat exchangers, is made possible in this way.

Very particular preference is given to a substream of the discharged substream of the condensed liquid being removed from the process. In this way, acrylic acid and further by-products, in particular the high-boiling by-products present in the organic phase II which are not stripped out with the organic phase II and the water of reaction formed, are discharged from the bottom section of the quenching stage and from the process. A constant liquid level in the bottom of the column and a largely constant proportion of by-products are achieved in this way.

Preference is likewise given, in the process of the invention, to a substream of the condensate present in the top section of the quenching stage B being discharged, preferably cooled to <20° C. and fed back into the top section of the quenching stage B, as a result of which the acrolein-containing gas stream coming in from the middle section of the quenching stage B is cooled and further condensate is continually produced and this is recirculated as runback to the middle section of the quenching stage (upper pump circulation). This allows, in particular, uniform introduction and temperature setting, in particular via external heat exchangers for condensation of aqueous and organic phase or solvent.

Preference is likewise given, in the process of the invention, to a substream of the condensate from the top section of the quenching stage B being fed to the phase separation I. As a result, the organic phase I can be separated off in-situ in a very simple and efficient way for immediate reuse in the process.

In the process of the invention, preference is also given to the phase separation I being carried out at a temperature of from 8 to 60° C., preferably from 10 to 50° C., particularly preferably from 12 to 40° C. This allows, in particular, optimal separation of the organic phase together with the solvent present with minimal losses.

According to the invention, preference is also given to a process in which the phase separation I is carried out with a residence time of from 0.5 to 20 minutes, preferably from 1 to 10 minutes. These conditions, too, contribute to optimal isolation of the organic phase together with the solvent present with minimal losses.

According to the invention, preference is also given to a process in which the aqueous fraction I from the phase separation I is at least partly added to the runback of the condensate produced from the quenching stage B. This largely prevents breakthrough of acrylic acid into the absorption stage and reduces the accumulation of solvent in the middle section of the quenching column.

According to the invention, preference is also given to a process in which the aqueous solution (sorption solution) which has been discharged from the distillation stage D and has been freed of acrolein and contains organic phase is partly recirculated directly to the top section of the absorption stage C and the remaining part is fed to the phase separation II.

The sorption solution from the distillation is in this way immediately utilized in-situ and virtually without losses and the total amount of waste streams is minimized. This mode of operation enables the residence time in the phase separation II to be set so that optimal isolation of the organic phase is made possible.

In addition to a sufficiently long residence time, selection of a suitable temperature is critical for the optimal function of the phase separator II operated according to the invention. Preference is therefore given to a process in which the phase separation II is carried out at a temperature of from 10 to 90° C., preferably from 15 to 60° C., particularly preferably from 20 to 40° C. This ensures optimal isolation of the organic phase together with the solvent present at the given viscosities with minimal losses.

Preference is also given, according to the invention, to a process in which the phase separation II is carried out with a residence time of from 0.5 to 20 minutes, preferably from 1 to 10 minutes. This likewise contributes to optimal isolation of the organic phase together with the solvent present with minimal losses and without the economics of the process suffering.

According to the invention, preference is additionally given to a process in which the amount of organic phase II introduced into the quenching stage B) is from 0.1 to 3% by weight, preferably from 0.2 to 1% by weight, based on the total amount of propene introduced into the reaction stage A). This ensures an optimal effect of the organic phase with minimal contamination by the additional streams introduced.

According to the invention, preference is also given to a process in which the aqueous fraction II from the phase separation II is partly recirculated to the absorption stage C), preferably to the top section of the absorption stage, and a further substream of the aqueous fraction II is preferably discharged from the process. In this way, the process water is utilized immediately and virtually without losses and the total amount of waste streams is minimized. The removal from the process controls the total amount of liquid in the process (hold-up) and avoids accumulation of by-products in the aqueous phase.

Preference is also given, according to the invention, to a process in which the content of organic phase in the sorption solution is from 0.1 to 5% by weight, preferably from 0.2 to 3% by weight. The content of solvent-containing organic phase is thus so high that an organic phase II which can be separated off is formed.

According to the invention, preference is also given to a process in which the sorption solution is introduced into the absorption stage C) at a temperature of 5-18° C., preferably 6-12° C., and at a pressure in the top section of the absorption stage C) in the range from 1.1 to 1.7 bar. This ensures substantial absorption of acrolein from the gas stream from the quench.

In the process of the invention, the quenching, absorption and/or distillation stages are preferably each configured in the form of a column. The advantage here is, inter alia, simple process operation, variable installation of packing or trays and thus matching to various boundary conditions of the process, e.g. throughputs, separation stages, etc. Preference is given to conventional columns containing ordered packing, columns containing random packing elements or tray columns such as bubble cap tray columns or sieve tray columns.

The process of the invention allows use of very small amounts of solvent compared to known processes, which amounts, when integrated into an existing acrolein plant, are recovered and reused without a large amount of additional apparatus or energy consumption, with the further previously mentioned positive effects on throughput and plant availability. This is of great economic and ecological advantage in an industrial-scale process.

DESCRIPTION OF THE EXAMPLE

Figure 1:
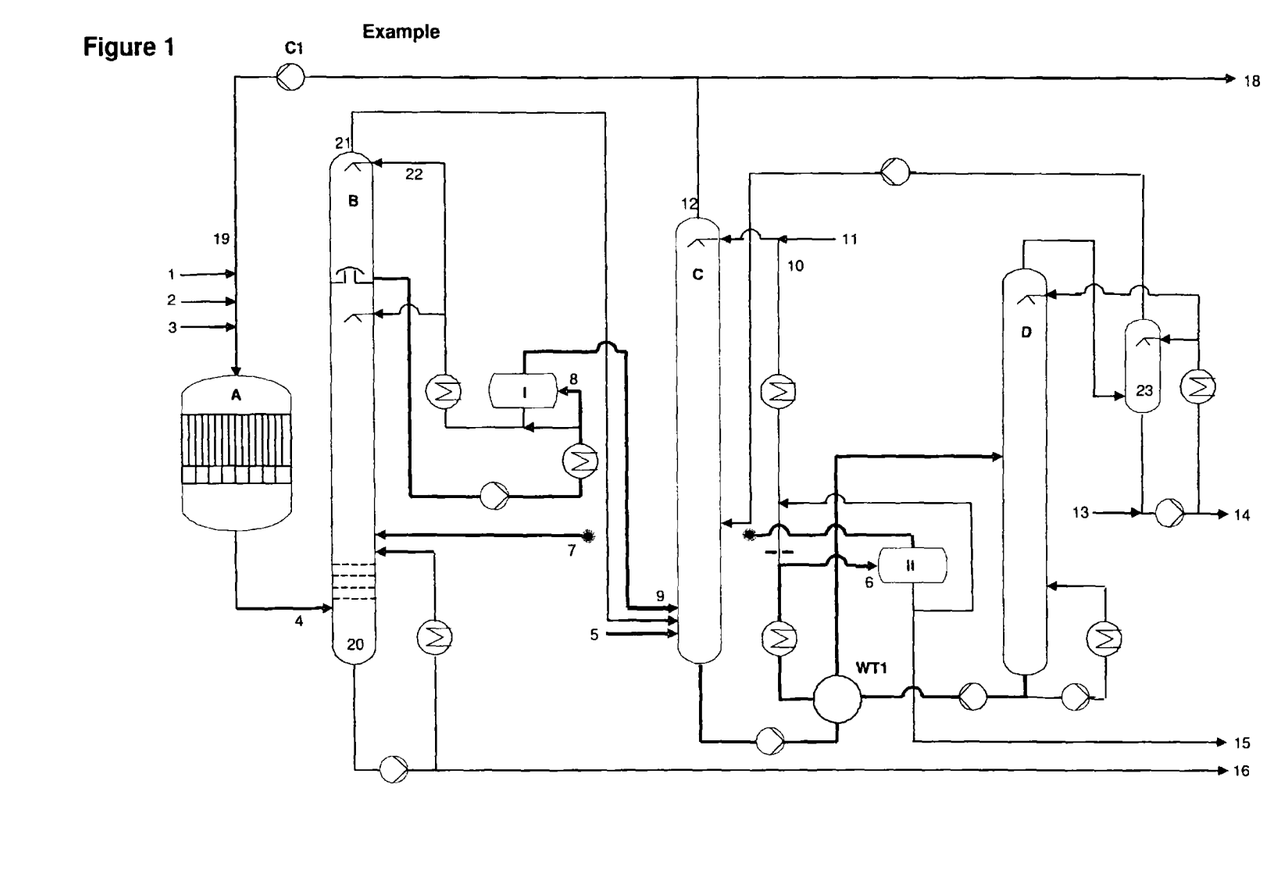

To illustrate the invention with the aid of the example, reference is made to FIG. 1 which shows an embodiment of the process of the invention.

Corresponding to the prior art, propene is firstly vaporized and the gaseous propene (3) is mixed with air (1), steam (2) and recycle gas (19, incondensable process gas=recirculated process offgas) and the mixture is fed into the shell-and-tube reactor (corresponding to step A). The conversion of the propene into acrolein and further by-products (reaction) then occurs there over suitable catalysts.

The process gas (4, reaction gas) leaving the bottom of the reactor is firstly freed of high boilers in a first column (with trays and ordered packing, hereinafter referred to as quenching column, corresponding to stage B). For this purpose, the incoming process gas at 220-250° C. is firstly cooled by means of a cooling circuit in the lower part of the column. In the middle part of the column, the high boilers, in particular acrylic acid, are then largely removed. Further cooling of the process gas travelling upward from the middle part of the column occurs in a cooling circuit in the upper part of the quenching column, with liquid being condensed out from the saturated gas stream and being recirculated as runback to the middle part of the column.

Corresponding to the prior art, the acrolein is then absorbed from the process gas exiting from the top of the quenching column in a subsequent column (with structured packing, hereinafter referred to as absorption column, corresponding to stage C). For this purpose, this process gas is fed into the bottom region of the absorption column and scrubbed with sorption solution coming from the top of the column, with the sorption solution becoming loaded with acrolein. The process gas which has been largely freed of acrolein leaves the plant as offgas (12) and is partly recirculated as recycle gas (19, diluent gas, recirculated process offgas) to make the feed mixture to the reactor inert.

Furthermore, corresponding to the prior art, the sorption liquid loaded with acrolein is drawn off from the bottom of the absorption column (corresponding to step C) and fed into approximately the middle of a distillation column (tray column, also referred to as desorption column, corresponding to step D). The acrolein is separated off there by distillation from the sorption solution. In the stripping section of the column, the sorption solution is largely freed of acrolein and can then be recirculated to the absorption column (10), with a small amount of deionized water (11) also being added to the sorption solution. In the enrichment section of the column, the acrolein is concentrated to close to the azeotropic point and the exiting acrolein vapour stream is condensed in an injection condenser (23) by means of supercooled acrolein to which stabilizer (13) is added and which circulates in a circuit. Hydroquinone or else other suitable stabilizers is/are generally used as stabilizer. The runback required for the separation is recirculated to the column and the acrolein obtained is fed to the acrolein tank farm (14).

This work-up process which corresponds in significant aspects to the prior art is now supplemented according to the invention by the two phase separators I and II in the top circuit of the quenching column and in the recirculation of the sorption solution (10) to the absorption column, and the mode of operation of the work-up process is altered according to the invention as per the further description.

An organic solvent which is sparingly soluble in water and forms an organic phase on mixing with water and preferably has a boiling point of 150-230° C., preferably 170-190° C. is added to the water which is usually used as sorption liquid. Furthermore, the solvent should preferably also have a good uptake capacity for oligomers formed and further organic by-products. 2-Ethylhexanol and the organic phases formed therewith have been found to be particularly well-suited for this purpose. To additionally introduce organic solvent, this is, for example, introduced in the lower region of the absorption stage C (5).

For the further purpose of the solvent, namely to separate off potentially polymer-forming impurities, the solvent matrix has to be purified. For this purpose, an organic phase II (SO II) is separated off by means of the phase separator II from the substream 6 of the sorption solution 6 recirculated to the absorption column (step C). Operation in a range of 10° C.-90° C. is maintained here, particularly advantageously in a temperature range of 15° C.-60° C. Accordingly, the phase separator II is installed in the process downstream of the heat exchanger designated as WT1. In WT1, the warm sorption liquid from the bottom of the desorption column is cooled by means of cold loaded sorption liquid from the bottom of the absorption column and the loaded sorption liquid is preheated before entry into the desorption column, in order to optimize energy integration.

The solvent-containing organic phase can be separated off from a substream of the sorption liquid, but it is also possible for all the recirculated sorption liquid to be passed through the phase separator II. The residence time (RST) in the phase separator II is determined by the volume of the completely flooded phase separator II and the volume flow of liquid passed through. Sufficiently good separation is achieved at residence times of 0.5-20 minutes, particularly preferably at an RST of 1-10 minutes, and this is accordingly set.

The organic phase II (SO II) separated off is then fed to the upper tray of the bottom circuit in the quenching column (step B) (7). The amount drawn off from the phase separator II is such that somewhat more liquid than the amount of SO II obtained in the phase separator II is drawn off and the formation of an interface in the phase separator II is thereby avoided. This has been found to be advantageous since increased formation of polymers occurs at the interface.

The volatile solvent matrix components are then stripped by means of the hot process gas from the organic phase II (7, SO II) fed to the bottom circuit of the quencher, in contrast to, the remaining high boilers, since SO II forms a second phase (principle of steam distillation). In the upper cooling circuit (including the top section), SO II largely condenses out with the remaining condensate at the lower temperatures and is then separated off from the cooling circuit via a phase separator I located in the upper cooling circuit (8). The organic phase I (SO I) which has been separated off is recirculated (9) to the bottom of the absorption column (step C). The operating parameters for the phase separator I equate in respect of the RST to those for phase separator II, but the operating temperature can be set lower since the SO I distilled off has a lower viscosity than the SO II loaded with high boilers from phase separator II.

This mode of operation allows a solvent flow which can be freely adjusted within a wide range in the depicted closed circuit through the hot part of the desorption column (step D) without any great solvent losses occurring. The amount which can be set is limited mainly by the distillation capacity in the quenching column. The content of SO is established in accordance with the amount of fresh solvent supplied and the losses of SO with the wastewater (15, 16) and the offgas (18). The SO content should be at least so high that an organic phase (comprising SO) is formed; excessively high SO concentrations in the sorption solution may cause a deterioration in the effectiveness of separation in the absorption column. For example, the SO content in the sorption solution is advantageously from 0.1 to 5% by weight, preferably 0.2-3% by weight.

The impurities taken up by the solvent remain in the bottom of the quenching column and are incinerated together with the wastewater. An advantage here is that the impurities are sufficiently readily soluble in the acrylic acid-containing wastewater (16) and no separate organic phase which could interfere in the subsequent incineration process as a result of fluctuating calorific value is formed. A further significant advantage of this process is that the apparatuses required for the process are utilized and no additional apparatuses are necessary for an external solvent work-up. The solvent consumption is reduced to such an extent that only comparatively small solvent losses in the offgas and in the wastewater have to be replaced.

A further advantage of this way of carrying out the process is that the solvent content before introduction of the sorption liquid into the absorption column and before introduction of the upper cooling circulation flow into the quenching column or the runback into the quenching column is reduced in terms of solvent content to such an extent that packings (as in the example) can be used at these places in the columns. At a given apparatus size, this is known to allow a higher throughput than when trays are used as column internals.

Experimental Description of the Comparative Examples 1 to 3

The comparative examples were carried out in a manner analogous to the above-described example but with the following differences:

FIG. 1: A process as per Example 1.

Figure 2:
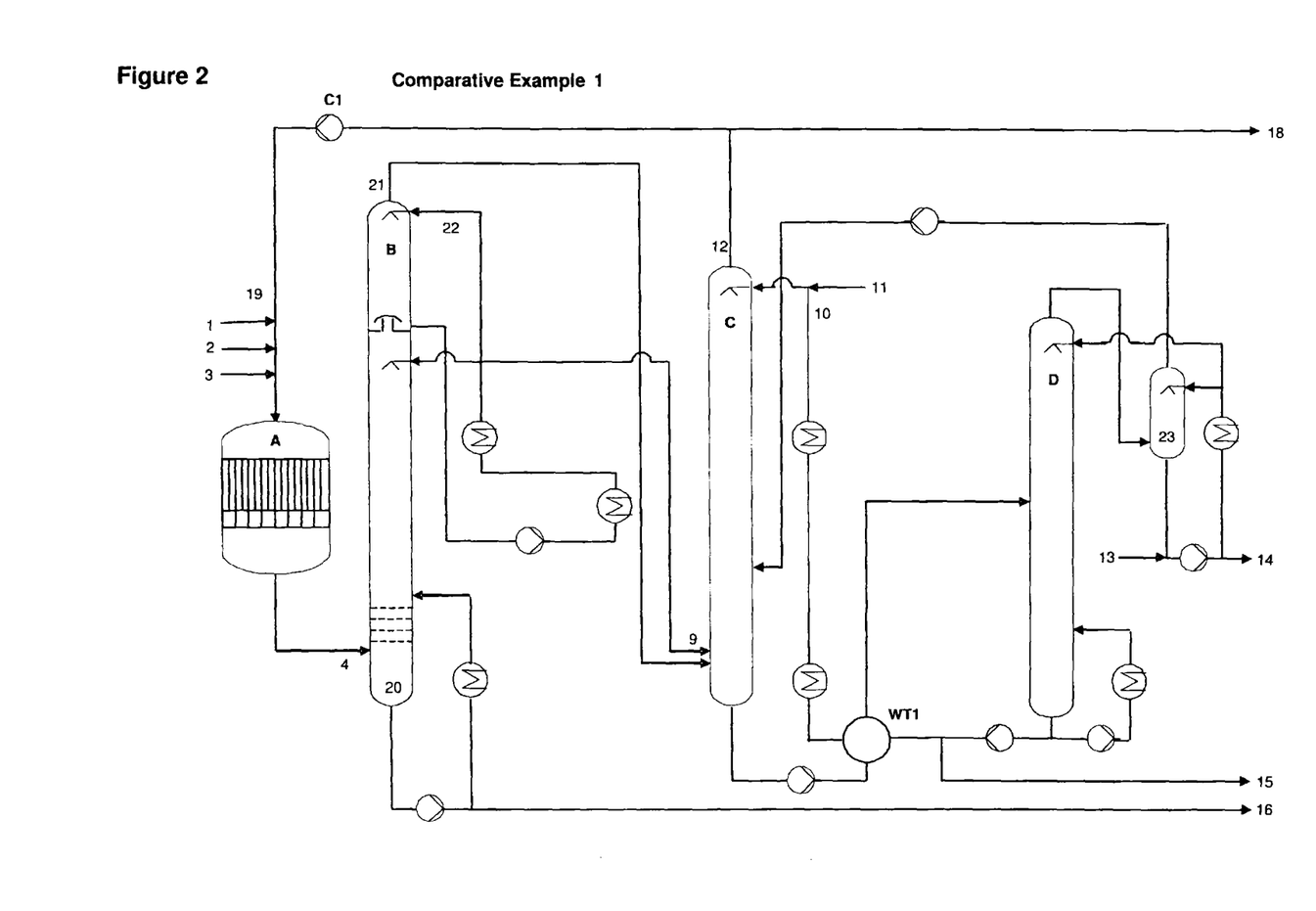

FIG. 2: In contrast to processes as per Example 1 (FIG. 1), the phase separator I and phase separator II are not installed in Comparative Example 1 and no solvent is introduced into the process.

Figure 3:
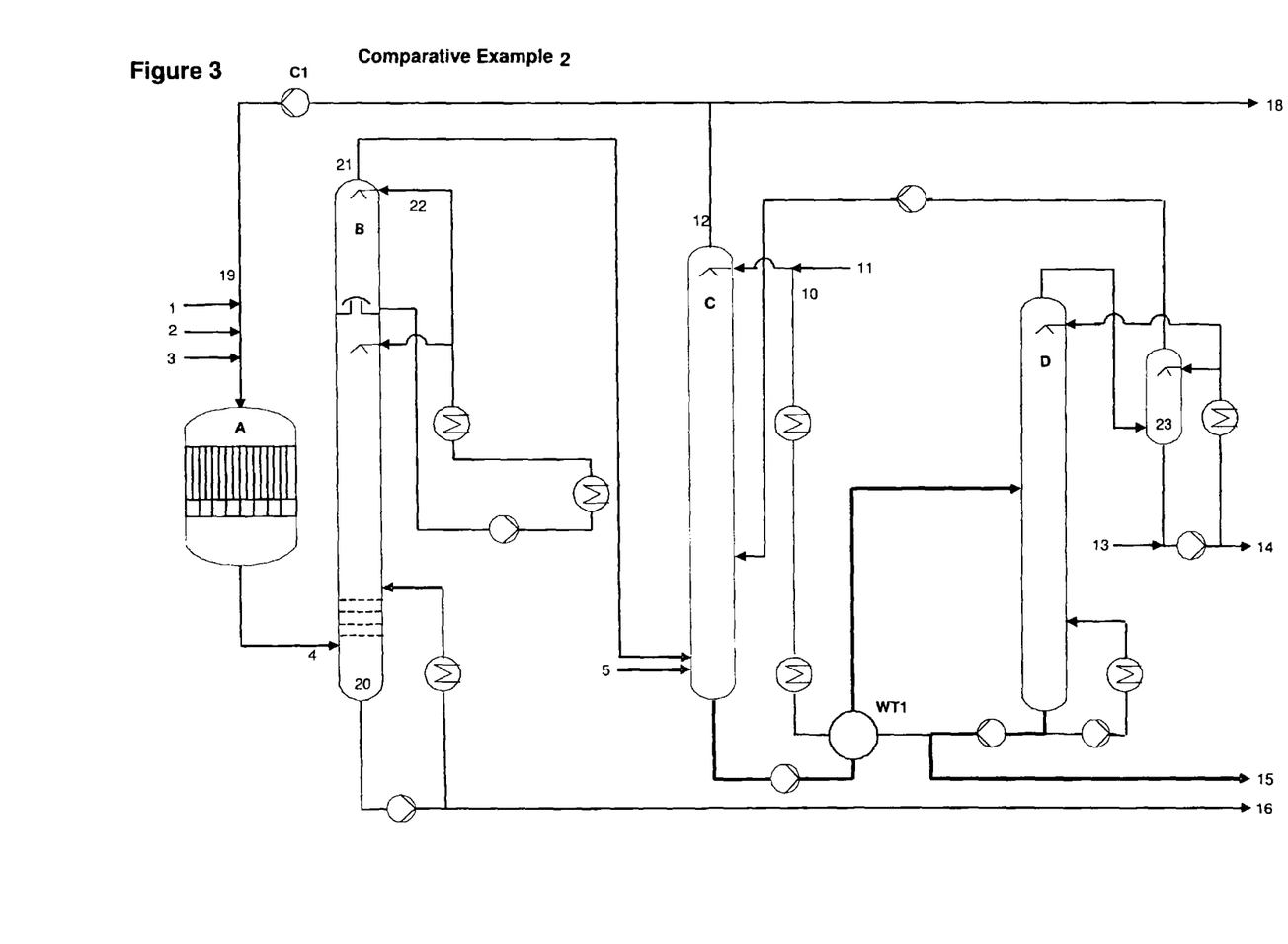

FIG. 3: In contrast to processes as per Example 1 (FIG. 1), the phase separator I and phase separator II are not installed in Comparative Example 2 and solvent is fed into the bottom of the absorption in the process. This accumulates to a certain extent in the sorption liquid and is removed as contaminated organic phase from the process together with the process wastewater from the sorption circuit (stream 15) and disposed of thermally.

FIG. 4: In contrast to processes as per Example 1 (FIG. 1), the phase separator II is installed in Comparative Example 3 and solvent is fed into the bottom of the absorption in the process. The organic phase II (SO II) drawn off from the phase separator II, which is operated as in Example 1, is fed to a 2-stage vacuum distillation. In a first stage, low boilers are separated off, and the distillable fraction of the SO is distilled off from high boilers in a second stage. This fraction is recirculated together with the fresh solvent (stream 5) back to the bottom of the absorption stage.

The process settings used in the examples (comparative examples) are summarized in Table 1.

TABLE 1

Process settings for the examples/comparative examples

| No. in the FIG. | Description | Unit | Example as per FIG. 1 | Comp. Example 1 as per FIG. 2 | Comp. Example 2 as per FIG. 3 | Comp. Example 3 as per FIG. 4 |
|---|---|---|---|---|---|---|
| 1 | Air (dry) | Standard m³/h | 28500 | 24000 | 28500 | 28500 |
| 2 | Steam | kg/h | 1500 | 1263 | 1500 | 1500 |
| 3 | Propene (Pe) | Standard m³/h | 3800 | 3200 | 3800 | 3800 |
| 4 | Process gas | ° C. | 240 | 240 | 240 | 240 |
| 5 | 2-Ethylhexanol | kg/h | 14 | | 30 | 30 |
|   | Distillate from ext. work-up | kg/100 kgPe kg/h | 0.2 n.a | n.a. | 0.4 n.a. | 0.4 70 |
| 6 | Sorption solution | m³/h | 67.5 | n.a. | n.a. | 67.5 |
|   | Temperature | ° C. | 25 | n.a. | n.a. | 25 |
|   | RST | min | 6 | n.a. | n.a. | 6 |
|   | Content of organic phase | % by weight | 0.3 | n.a. | n.a. | 0.5 |
| 7 | Organic phase from phase separator II | kg/h kg/100 kgPe | 60 0.8 | n.a. | n.a. | n.a. |
| 8 | Cooling circulation flow | m³/h | 60 | n.a. | n.a. | n.a. |
|   | Temp. | ° C. | 20 | n.a. | n.a. | n.a. |
|   | RST | min. | 6 | n.a. | n.a. | n.a. |
| 9 | Organic phase from phase separator I | kg/h kg/100 kgPe | 40 0.6 | n.a. | n.a. | n.a. |
| 10 | Sorption solution | m³/h ° C. | 135 8 | 120 8 | 135 8 | 135 8 |
| 11 | Deionized water | m³/h | 1.2 | 1.2 | 1.2 | 1.2 |
| 12 | Pressure at the outlet from the absorption stage | bara | 1.3 | 1.3 | 1.3 | 1.3 |
| 13 | Stabilizer (10% hydroquinone in acrolein) | kg/h | 50 | 42 | 50 | 50 |

TABLE 1-continued

Process settings for the examples/comparative examples

| No. in the FIG. | Description | Unit | Example as per FIG. 1 | Comp. Example 1 as per FIG. 2 | Comp. Example 2 as per FIG. 3 | Comp. Example 3 as per FIG. 4 |
|---|---|---|---|---|---|---|
| 14 | Acrolein | kg/h | 8000 | 6737 | 8000 | 8000 |
| 15 | Wastewater from the sorbate circuit | t/h | 1.2 | 1.2 | 1.2 | 1.2 |
| 16 | Wastewater from the quenching stage | t/h | 5.4 | 4.6 | 5.4 | 5.4 |
| 17 | Organic phase from phase separator II to external work-up | kg/h | n.a. | n.a. | n.a. | 100 |
| 18 | Process offgas to incineration | Standard $m^3$/h | 25600 | 21600 | 25600 | 25600 |
| 19 | Recirculated process offgas | Standard $m^3$/h | 22000 | 18560 | 22000 | 22000 |
| 20 | Temperature at the bottom of the quencher | °C. | 70 | 70 | 70 | 70 |
| 21 | Pressure at the top of the quencher | bara | 1.5 | 1.5 | 1.5 | 1.5 |
| 22 | Temperature in the top circuit of the quencher | °C. | 14 | 14 | 14 | 14 | n.a.: not applicable

Results of the Examples/Comparative Examples

The examples/comparative examples described were each carried out in a plant corresponding to the plants shown in FIGS. 1 to 4. The results reported are determined essentially by the parameters described.

FIG. 1 Process according to the invention Plant operation for >1 year until cleaning becomes necessary Specific solvent consumption about 0.2% by weight of fresh solvent based on the amount of propene used Comparative Examples 1-3

FIG. 2 It is found here that the maximum plant load (i.e. Pe fed in) which can be set is limited to about 80% of the plant load in Example 1. At a higher load, the operating behaviour of the plant becomes unstable due to foam formation in the distillation. Furthermore, it is observed that, even at this lower load, cleaning of the bottom region of the distillation becomes necessary after not more than 3 months (formation of polymer deposits). No solvent consumption.

FIG. 3 It is found that in this case a reduction in production due to foam formation in the distillation is no longer necessary and that the cleaning interval for the production plant is extended to up to 6 months. The fresh solvent consumption is 0.4% by weight of solvent based on the amount of propene used.

FIG. 4 It is found here that plant operation as in Example 1 is made possible, but the fresh solvent consumption is 0.4% by weight of solvent based on the amount of propene used. The capital costs for the vacuum distillation plant are substantially higher than for the phase separator I and operation is susceptible to malfunction because of the tar-like consistency of the distillation residue.

TABLE OF REFERENCE NUMERALS

| No. in the FIGS. | Description |
|---|---|
| 1 | Air (dry) |
| 2 | Steam |
| 3 | Propene |
| 4 | Process gas |
| 5 | 2-Ethylhexanol Distillate from ext. work-up |
| 6 | Sorption solution |
| 7 | Organic phase from phase separator II |
| 8 | Cooling circulation flow |
| 9 | Organic phase from phase separator I |
| 10 | Sorption solution |
| 11 | Deionized water |
| 12 | Pressure at the outlet from the absorption stage |
| 13 | Stabilizer (10% hydroquinone in acrolein) |
| 14 | Acrolein |
| 15 | Wastewater from the sorbate circuit |
| 16 | Wastewater from the quenching stage |
| 17 | Organic phase from phase separator II to external work-up |
| 18 | Process offgas to incineration |
| 19 | Recirculated process offgas |
| 20 | Temperature at the bottom of the quencher |
| 21 | Pressure at the top of the quencher |
| 22 | Temperature in the top circuit of the quencher |
| 23 | Injection condenser |
| WT1 | Heat exchanger 1 |

The invention claimed is:

1. Continuous process for preparing acrolein, wherein the following are carried out
   A) gas-phase oxidation of propene by air over a heterogeneous catalyst in the presence of a diluent gas in one reaction stage
   B) capture of the acrolein-containing gas stream A) in a quenching stage consisting of bottom, middle and top sections for separating off by-products in the presence of water and an organic phase containing sparingly water-soluble organic solvent C) capture of the acrolein-containing gas stream from the quenching stage B) in an absorption stage consisting of bottom, middle and top sections in the presence of water and an organic phase containing sparingly water-soluble organic solvent to obtain an aqueous acrolein solution which contains organic phase, and an incondensable gas stream C1) at least partial recirculation of the incondensable gas stream from C) as diluent gas to the reaction stage A)

D) separation of the acrolein by distillation from the aqueous acrolein solution which contains organic phase from C) in a distillation stage where the remaining aqueous solution which contains organic phase and has been freed of acrolein is discharged from the distillation stage D) so as to form an organic phase II which is separated from the associated aqueous fraction II (phase separation II), the organic phase II is introduced into the bottom section of the quenching stage B) from which the organic phase II is separated off together with an aqueous fraction via the top section by distillation and/or stripping so as to form an organic phase I which is separated from the associated aqueous fraction I (phase separation I) and introduced into the bottom section of the absorption stage C).

2. Process according to claim 1, wherein organic solvent which is sparingly water-soluble is introduced continuously or intermittently to supplement the organic phase at a suitable point in the process.

3. Process according to claim 2, wherein the organic solvent is introduced into the bottom section of the absorption stage and/or of the distillation stage.

4. Process according to claim 2, wherein an organic solvent which has a boiling point at atmospheric pressure of from 150 to 230° C. is used.

5. Process according to claim 4, wherein a branched or unbranched open-chain C6- to C10-alcohol is used as organic solvent.

6. Process according to claim 2, wherein a further amount of from 0.05 to 1% by weight of organic solvent, based on the amount of propene introduced into the reaction stage A), is added.

7. Process according to claim 1, wherein the acrolein-containing gas stream from A) enters at a temperature of 200-280° C. into the bottom section of the corresponding B).

8. Process according to claim 1, wherein the temperature at the bottom of the quenching stage B is set in the range from 60 to 90° C. at a pressure in the top section of from 1.2 to 1.8 bar so that no separate organic phase is present in the bottom section of the quenching stage B.

9. Process according to claim 8, wherein the temperature at the bottom of the quenching stage B is set by discharging a substream of the liquid condensed there and, after appropriate cooling, feeding it back into the lower third of the quenching stage B (lower pump circulation).

10. Process according to claim 9, wherein a substream of the discharged substream of the condensed liquid is removed from the process.

11. Process according to claim 1, wherein a substream of the condensate present in the top section of the quenching stage B is discharged and fed back into the top section of the quenching stage B, as a result of which the acrolein-containing gas stream coming in from the middle section of the quenching stage B is cooled and further condensate is continually produced and this is recirculated as runback to the middle section of the quenching stage (upper pump circulation).

12. Process according to claim 11, wherein a substream of the condensate is fed to the phase separation I.

13. Process according to claim 1, wherein the phase separation I is carried out at a temperature of from 8 to 60° C.

14. Process according to claim 1, wherein the phase separation I is carried out with a residence time of from 0.5 to 20 minutes.

15. Process according to claim 11, wherein the aqueous fraction I from the phase separation I is at least partly introduced into the runback of the condensate produced.

16. Process according to claim 1, wherein the aqueous solution (sorption solution) which has been discharged from the distillation stage D and has been freed of acrolein and contains organic phase is partly recirculated directly to the top section of the absorption stage C and the remaining part is fed to the phase separation II.

17. Process according to claim 1, wherein the phase separation II is carried out at a temperature of from 10 to 90° C.

18. Process according to claim 1, wherein the phase separation II is carried out with a residence time of from 0.5 to 20 minutes.

19. Process according to claim 1, wherein the amount of organic phase II introduced into the quenching stage B) is from 0.1 to 3% by weight based on the total amount of propene introduced into the reaction stage A).

20. Process according to claim 1, wherein the aqueous fraction II from the phase separation II is partly recirculated to the absorption stage C).

21. Process according to claim 1, wherein the content of organic phase in the sorption solution is from 0.1 to 5% by weight.

22. Process according to claim 16, wherein the sorption solution is introduced into the absorption stage C) at a temperature of 5-18° C. and at a pressure in the top section of the absorption stage C) in the range from 1.1 to 1.7 bar.

23. Process according to claim 1, wherein the quenching, absorption and/or distillation stages are each configured in the form of a column.

* * * * *